United States Patent [19]

Tan et al.

[11] Patent Number: 4,725,544
[45] Date of Patent: Feb. 16, 1988

[54] METHOD FOR PURIFYING XYLANASE

[76] Inventors: Larry U. Tan, 8-73 Woodridge Cres., Nepean, Ontario, Canada, K2B 7T2; John N. Saddler, 915 River Road, Ottawa, Ontario, Canada, K1K 3J2; Ernest K. Yu, 6272 Fortune Dr., Gloucester, Ont., Canada, K1C 2B1

[21] Appl. No.: 856,934

[22] Filed: Apr. 25, 1986

[51] Int. Cl.$^4$ ............... C12N 9/24; C12N 9/42; C12R 1/885
[52] U.S. Cl. ................. 435/200; 435/209; 435/814; 435/945
[58] Field of Search ............. 435/200, 209, 814

[56] References Cited

U.S. PATENT DOCUMENTS 4,275,159  6/1981  Puls et al. ............... 435/175

OTHER PUBLICATIONS

Fournier et al, Biotechnology and Bioengineering, vol. 27, pp. 539–546 (1985).

Primary Examiner—Lionel M. Shapiro
Attorney, Agent, or Firm—Trevor C. Klotz

[57] ABSTRACT

The separation of xylanases from mixtures thereof with other hemicellulases, particulary cellulase produced by the culturing of hemicellulolytic microorganisms, particularly the fungus *Trichoderma harzianum* E58 and *Trichoderma reesei* by ultrafiltration through an ultrafiltration membrane having a low molecular weight cut-off point in the range of about 1,000 to 20,000 daltons to obtain a cellulase rich retentate and xylanase rich ultrafiltrate. The dilute xylanase rich filtrate from the ultrafiltration is concentrated and purified by adsorption and elution from an insoluble matrix, e.g. a cationic exchange resin. The xylanase obtained is suitable for use in the hydrolysis of hemicellulose for which it is selective, particularly in the presence of cellulose and the cellulase rich retentate is suitable for the hydrolysis of cellulose.

13 Claims, 4 Drawing Figures

METHOD FOR PURIFYING XYLANASE

BACKGROUND OF THE INVENTION

1. Field of Invention

The present invention relates to the separation of hemicellulases from a mixture thereof. In particular the present invention relates to the separation of xylanase from a mixture thereof from other hemicellulases, particularly cellulase to produce a xylanase rich fraction which is subsequently purified and concentrated and is particularly useful in the hydrolysis of hemicelluloses for which it is selective and thus is useful for hydrolysing hemicelluloses in the presence of celluloses. Also produced is a concentrated cellulase rich fraction which is useful in the hydrolysis of cellulose.

2. Description of the Prior Art

Lignocellulose, the world's largest renewable biomass resource is composed mainly of lignin, cellulose and hemicellulose, of which the large part of the latter is xylan. Much of the current research and development has been directed towards the utilization of the cellulose fraction for liquid fuel production. However if value-added products could be obtained from the hemicellulose and lignin streams, economics of the process could be significantly improved. Applicants are presently developing a process for the production of fuel and chemicals from lignocellulosics. In the process lignocellulosics are first pretreated with steam then fractionated into hemicellulose and lignin streams. Both cellulose and hemicellulose are potential sources of sugar for fermentation into valuable products. Thus for a number of years the applicants have been developing a process where aspenwood chips are first steam pretreated to enhance their subsequent enzymatic hydrolysis to fermentable sugar. As disclosed in Saddler, et al (1983) Biotechnol. Bioeng. Symp. 13, 225-238, the hemicellulose, lignn, and cellulose streams were then separated by selectively extracting the pretreated material with water and dilute alkali. The cellulose and hemicellulose streams were then respectively hydrolysed by cellulases and xylanases and fermented to ethanol and 2,3-butanediol by the appropriate microorganisms.

It had further been shown that high levels of cellulase and xylanase enzymes were efficiently produced by the fungus *Trichoderma harzianum* E 58 as disclosed by Yu, et al (1984) Biotechnol. Bioeng. Symp. 14, 341-352. As the hemicellulose and cellulose derived sugars are normally utilized by different microorganisms for various products, the hemicellulose and cellulose fractions are routinely separated into different streams in the above process and thus if an inexpensive process is available for the separation of the xylanase complex from the cellulase complex two enzyme streams could be efficiently utilized for the hydrolysis of the hemicellulose and cellulose streams, respectively, while reducing the overall cost of separate enzyme production steps.

D-xylanases have been purified from many sources using various combinations of techniques such as ion-exchange chromatography, gel permeation chromatography, isoelectric focusing, zone electrophoresis, affinity binding and crystallization. Attention is directed to the article of Dekker, R. F. H. and Richards, G. N. (1976) Adv. Carbohydrl Chem. Biochem. 32, 277-352. However the described procedures are deficient in that they are either too slow, too cumbersome to use, too difficult to scale up or too expensive to incorporate into the production scheme for a bulk enzyme. Alternatively, others as disclosed by Paice, M. G. et al (1984), J. Wood Chem. Technol. 4, 187-198 have used ethanol to selectively separate the xylanase from the cellulase components but this required very high concentrations of ethanol and the purified xylanases still contained approximately 3% cellulase. In addition, the use of organic solvents necessitates the need for the wastewater treatment, and devices for the removal of toxic and explosive vapours as well as explosive proof motors and switches as disclosed by Volesky, B. et al (1985) CRC Crit. Rev. Biotechnol 2 119-146. These can all add to the capital and processing costs. Still others have prepared small amounts of cellulase-free xylanase by cloning the xylanase gene into non-cellulolytic microorganisms as disclosed in the poster session at the Pulp and Paper Research Institute of Canda, Pointe Claire, Quebec, 1985. The problems associated with this approach is that the xylanase enzyme synthesized by the new host is usually located intracellularly. The extraction of the xylanase enzyme from inside the cell is difficult, time-consuming, expensive and results in low yield. The xylanase, unless fractionated by a series of complicated procedures, will be of low specific activity and may contain proteases which may destabilize the xylanase activities. Thus processes for the purification of enzymes including xylanases are already available. However, these processes suffer from being cumbersome, requiring many steps which generally result in low recoveries. The processes are often time consuming with low yields of the product xylanase (milligram quantities). These processes are mainly designed for the preparation of small amounts of xylanase, irrespective of the cost in time and money for the purposes of analytical studies. Such processes are not feasible if the xylanase is to be used on an industrial scale. Purification processes are disclosed by Frederick, et al in an article entitled "Purification and Characterization of Endo-xylanases from *Aspergillus niger*" Biotechnology and Bioengineering, Vol. 27, pages 525-532 (1985). Again reference is made to an article entitled "Xylan-Degrading Enzymes of the Yeast *Cryptococcus albidus*" by Biely, et al in European Journal of Biochemistry, 108, pages 313-321 and an article of "Isolation and Characterization of a Xylanase from *Bacillus subtilis*, Vol. 46 No. 2, Applied Environmental Microbiology, Aug. 1983, pages 511-514, a further article entitled "Purification and Some Properties of an Endo 1,4-$\beta$-D-xylanase from Streptomyces sp, by Tasuku Nakajima, et al in the Journal of Ferment. Technol. Vol. 62, No. 3, pages 269-276, 1984, an article entitled "Purification and Some properties of Xylanase from *Cryptococcus flavus* by Nakanishi, et al, Journal of Ferment. Technol. Vol. 62, No. 4, pages 361-369, 1984 and an article entitled Isolation, Purification and Some of the Properties of Hemicellulase from Fusarium Sp.by Wankhede, et al, Carbohydrate Research, 96 (1981) pages 249-257.

SUMMARY OF THE INVENTION

The present invention provides a simple process for the separation of xylanase at high purity from a mixture thereof with other hemicellulases, particularly cellulase, which requires only low quantities of consumables and has rapid process rates. The present invention also provides such a process in which the separated xylanases obtained in high yield of about 80% compared with that obtained in the prior art of about 50%. The present invention also provides such a process which can be operated on an industrial scale to produce large quantities of separated xylanase in a relatively short period of time of 16 hours as compared to 1 week and thus provide a process for the bulk production of purified xylanase. The present invention provides a simplified process for the bulk preparation of concentrated cellulase-free hemicellulases produced by the culturing of hemicellulolytic microorganisms such as Trichoderma harzianum or Trichodurma reesei with or without a concomitant production of concentrated cellulase rich fraction.

According to the present invention there is provided a process for the separation of xylanase from a mixture thereof with other hemicellulases, said mixture being produced by the culturing of hemicellulolytic microorganisms which comprises subjecting said mixture to ultrafiltration through an ultrafiltration membrane having a low molecular weight cut-off point between 1,000 and 20,000 daltons to obtain a xylanase rich ultrafiltrate, and concentrating and purifying the ultrafiltrate by adsorption and elution from an insoluble matrix to produce a highly purified concentrated xylanase.

In a particularly preferred embodiment of the present invention there is provided a process for the separation of xylananse from a mixture thereof with cellulase, said mixture being produced by the culturing of hemicellulolytic microorganisms which comprises subjecting said mixture to ultrafiltration through an ultrafiltration membrane having a low molecular weight cut-off point between 1,000 and 20,000 daltons to obtain a xylanase rich ultrafiltrate and a cellulase rich retentate, and concentrating and purifying the ultrafiltrate by adsorption and elution from an insolube matrix to produce a highly purified concentrated xylanase.

The combination of the steps of ultrafiltration of the culture filtrate through an ultrafiltration membrane with a low molecular weight cut-off point between 1,000 and 20,000, preferably between 5,000 and 20,000 and more preferably between 5,000 and 15,000 to produce a purified ultrafiltrate containing the xylanases in high yield with high activity with a subsequent high purification of the ultrafiltrate by ion exchange with an insoluble matrix preferably a cationic exchanger, in particular a SP-ZetaPrep cartridge forms the basic concept of the present invention. It is based on the surprising discovery that although the xylanases in the culture filtrate have molecular weights substantially above 20,000 they will pass in high yields and at high activity through an ultrafiltration membrane having a low molecular weight cut-off point of less than 20,000 daltons, and more preferably less than 15,000 and suitably not more than 10,000.

It will be recognized that the lower the molecular weight cut-off point of the ultrafiltration membrane the purer will be the ultrafiltrate as the less the high molecular weight contaminants of the ultrafiltrate, e.g. the cellulases will pass therethrough. This high purity in the ultrafiltrate allows the ultrafiltrate to be further purified to a very high purity such as will allow it to be used in high technical processes, as such preferential hydrolysis to eliminate the xylan component from cellulose pulp in which the presence of cellulases even in very small amounts is undesirable, by adsorption on an insoluble matrix, particularly a cationic exchange membrane with elution therefrom. This further purification is very efficient and rapid process as compared with that of a second ultrafiltration of the ultrafiltrate from an ultrafiltration membrane of molecular weight of 30,000 through a membrane of molecular weight of 300 to 700 as disclosed in U.S. Pat. No. 4,275,159 Puls et al issued June 23, 1981. This patent describes the use of an ultrafiltration membrane with a molecular weight cut-off point of 30,000 daltons to separate xylanase (filtrate) from other proteins (supernate or retentate) followed by concentration using ultrafiltration using a 500 dalton membrane. The majorty of xylanases are small proteins often with molecular weights less than 30,000 daltons. It is not surprising that xylanases can penetrate this membrane. The present invention is predicated on the discovery that despite the xylanases having a molecular weight equal to or greater than 20,000 daltons they could penetrate a ultrafiltration membrane with a low molecular weight cut-off point of less than 20,000 daltons. As the result of the low-molecular weight cut-off point of less than 20,000 daltons in the process of the present invention as well as the use of the ion exchange step the xylanase has virtually no cellulases which is important for their use to preferentially hydrolyse and eliminate the xylan component from the cellulose pulp. The ion exchange step of the present invention is faster and more efficient than the ultrafiltration step of the U.S. patent using membranes with molecular weight cut-off points of less than 1,000. In addition the ion exchange step also further purifies the xylanase from the contaminating cellulase component as well as the elimination of soluble sugars. Thus the ultrafiltration of the U.S. patent with the low-molecular weight membrane is slow and as the xylanase is withheld by the membrane, inefficient both with regard through purity and yield in the final ultrafiltrate inter alia due to the initial ultrafiltrate itself obtained from the membrane of molecular weight 30,000 having substantial impurities such as of the cellulases.

The hemicellulolytic microorganism includes fungi and bacteria. In particular mention may be made of the fungi *Trichoderma harzianum* E58 and *Trichoderma reesei* and *Thermoascus aurantiacus* strain C436 all of which are deposited in the culture collection of Forintek Canada Corporation, Ottawa, Canada. Particularly good results are obtained with the fungus *Trichoderma harzianum* E58. The culture collection is registered as Collection No. 38 under Dr. J. N. Saddler of Forintek Canada Corp., Eastern Forest Products Laboratory in the *World Directory of Collections of Microorganisms*, edited by Vicki F. McGowan and V. B. D. Skerman, second edition, pp. 13, 1982 published by the World Data Center, Univeristy of Queensland, Brisbane, Australia. The fungus, *Trichoderma harzianum* E58 was also deposited in the internationally recognized organization, American Type Culture. Collection, 12301 Parklawn Dr., Rockville, Md. 20852-1776 and filed as *Trichoderma viride* 32086. The enzymes produced by the Thermoascus source are thermally stable which is a very desirable property in lignocellulose hydrolyses. In particular the mixture, is suitably a culture filtrate obtained by culturing *Trichoderma harzianum* E58 in a salt solution containing cellulose or hemicellulose as carbon source and subjecting the culture obtained to filtration or centrifugation to produce the culture filtrate.

The ultrafiltration membrane is one having a low molecular weight cut-off point between 1,000 and 20,000 daltons. At the lower limits xylanase retained does not pass through the ultrafiltration membrane, while at the high limit the hemicellulases, particularly the cellulase will start to pass through the membrane into the ultrafiltrate to produce an unacceptable purity for subsequent ion exchange purification. Desirably the ultrafiltration membrane has a low molecular weight cut-off point between 1,000 and 20,000 or preferably a low molecular weight cut-off point has a maximum of 12,000 and is suitably about 10,000. Suitably the membrane is a noncellulosic and preferably a polysulfone membrane.

According to the present invention the ultrafiltrate containing the xylanase is concentrated and purified by adsorption and elution from an insoluble matrix to produce a highly purified xylanase. This produces an essentially cellulase-free concentrated xylanase solution. Such a purified cellulase-free xylanase solution may be used, for example, for the removal of contaminating hemicellulose components from high grade cellulose pulps. Thus, other procedures as disclosed by Paice, et al (1984) J. Wood Chem. Techol. 4, 187-198 have been partially successful in reducing the amount of hemicellulose in aspen mechanical pulps using purified xylanase from *Schizophyllum commune*. Unfortunately the viscosity of the pulp was also reduced, possibly because of the relatively high concentration, approximately 3%, of contaminating endoglucanase activity that was present in the preparation. In addition the cost of producing the xylanase was high since the process depended on fractional precipitation using a volume ratio of 3 to 1 ethanol to culture filtrate. The inexpensive process of the present invention which produces virtually cellulase-free xyalanase is more amenable to this application and may also be used for the manufacture of liquid coffee, the adjustment of wine characteristics and for the enhancement of astaxanthin (3,3'-di-hydroxy-4,4'-diketo-beta-carotene) extraction. It may also be used in the food industry for the clarification of fruit juices. Thus, the commercial application of the purified and concentrated xylanase produced by the process of the present invention is useful for the selective removal of contaminating hemicellulose from high-grade cellulose pulps used in the manufacture of rayon and cellophane. The purified xylanase may also be used to reduce the amount of hemicellulose in aspen mechanical pulps. Cellulase rich components may be used for the combined hydrolysis and fermentation of lignoncellulosics to liquid fuels and chemicals. The cellulase rich fraction may also be used in the manufacture of liquid coffee, clarification of fruit juices and in the alcohol beverage industry for enhancing recovery in the distillation step.

The ultrafiltration step is a rapid, efficient and inexpensive procedure and can be easily scaled up to an industrial level of production. It is found to be very selective in preventing the penetration of all proteins except the xylanase enzyme. The resulting xylanase enzymes in the filtrate are virtually free from cellulases. This step also eliminates the particulate which may interfere with the subsequent step, namely the concentration of the xylanase enzymes by adsorption and elution. The resultant xylanase fraction is pure and is concentrated in a low salt buffer while the concentrated cellulase rich fraction contains adequate amounts of both cellulase and xylanase enzymes for effective cellulose-hemicellulose hydrolysis. Adsorption may be done with a variety of adsorbants including hydrophobic, cationic as well as anionic exchangers, although the best method appears to be the process which uses a cationic exchanger, binding the xylanase at pH 4 at low salt concentrations and elution by change in pH. This method of elution is important in minimizing the salt concentration in the final xylanase preparation. The pure xylanase fraction will be used for the selective removal of hemicellulose without affecting the cellulose component. In one embodiment of the present invention the ultrafiltrate may be diluted and the pH is adjusted to between 3-5 with acid passed through an SP-ZetaPrep column with a buffer between pH of 3 to 5 and eluted with buffer between pH of 7 to 10.

The process of the present invention results in the production of xylanase enzymes which are of high specific activity (2,100 IU/mg protein) and high purity (cellulase activity: xylanase activity =1:1,000,000 with no other non-xylanase proteins) with a yield of 77%. Only approximately 3% of the xylanase enzymes are lost in the process. The remaining 20% are retained in the cellulase rich fraction concentrated by 8 to 10 fold relative to their concentrations in the culture filtrate. The cellulase rich component is concentrated as a result and may be used independently of the pure xylanase fraction. The process is efficient, simple and may be easily scaled up using relatively simple equipment and unlike ethanol precipitation method no special precautions associated with explosive chemicals are necessary. Thus, in the process of the present invention, for example, the fungus *Trichoderma harzianum* E58 is grown in a salt solution containing cellulose or hemicellulose as carbon source. Maximum accumulations of xylanase and/or cellulase activity is usually three to six days. The culture is filtered or centrifuged to obtain the culture filtrate. The culture filtrate is ultrafiltrated with a noncellulose membrane with a molecular weight cut-off point of around 10,000 daltons. Typically the ultrafiltration step is stopped when the retentate is reduced to 1 to 2% of original volume. The retentate is referred to as the cellulase-rich fraction containing the cellulase enzymes which are concentrated by 40 to 60 fold. This fraction also contains approximately 20% of the original xylanase activities which are concentrated by approximately 8 to 10 fold. 80% of xylanase activities which are found in the ultrafiltrate are concentrated and desalted by adsorption onto a cationic exchanger. Typically the ultrafiltrate is diluted with an equal volume of water and the pH is adjusted to 4 with acetic acid. The dilution is then pumped through a SP-ZetaPrep column, washed with a 10 mM sodium acetate buffer, pH4 and the xylanase activities are eluted with a 50 mM sodium phosphate buffer, pH8. Selective pooling results in xylanase activities concentrated by approximately 34 fold relative to the ultrafiltrate. Thus a process is provided for the bulk purification of cellulase free beta-1,4-xylanase from inter alia the fungus *Trichoderma harzianum* E58. The process involves the primary step of ultrafiltering culture filtrate via a 10,000 molecular weight cutoff membrane to separate the cellulase retentate and the xylanase ultrafiltrate fractions. The cellulase component was concentrated by 40 to 60 fold resulting in an enzyme complex which could effectively hydrolyse high concentrations of cellulose to glucose. The xylanase was concentrated and solvent exchanged by adsorption to a cationic exchanger SP-ZetaPrep 250 followed by elution with a pH change in the buffer to give a purified and concentrated xylanase enzyme complex dissolved in a low salt buffer. The resultant xylanase system was pure by the criteria of sodium dodecyl sulphate polyacrylamide gel electrophoresis, has a very high specific activity of 2,100 IU/mg protein, was virtually free of filter paper activity and had a ratio of contaminating endoglucanase activity of $10^{-6}$. Approximately 3.3 gm of protein which contained in excess of 7,000,000 IU of xylanase activity was obtained from 17 liters of original culture filtrate processed adaptable to scale up to an industrial scale level of production.

The adsorption step on an insoluble matrix performs more than just concentrating the xylanase. It removes the trace amount of cellulase which is still present in the xylanase preparation after the ultrafiltration. Such thorough removal of cellulase is important if the xylanase is to be used for the removal of hemicellulose from cellulose pulp for the manufacture of high volume material such as rayon, cellophane, cellulose and cellulose acetate. A small amount of contaminating cellulase (endoglucanase) would partially hydrolyse the cellulose fibres resulting in lower viscosity pulp which is an undesirable process.

BRIEF DESCRIPTION OF THE DRAWINGS

The present invention will be further illustrated by way of the following Example in conjunction with the accompanying drawings, in which.

DETAILED DESCRIPTION OF PREFERRED EMBODIMENTS

EXAMPLE

Figure 1:
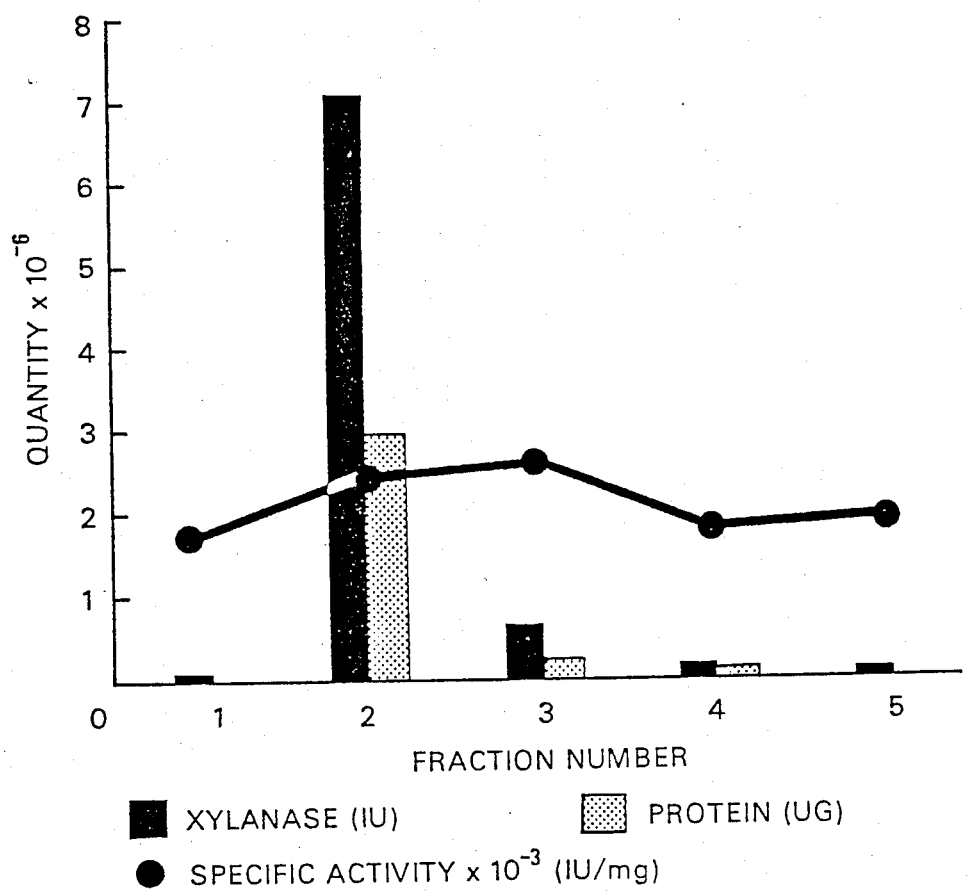
FIG. 1 is an elution profile of SP-ZetaPrep 250 column charged with six million IU of xylanase activity (3.3, g of protein). Fractions of 250 ml were collected.

*Culture conditions:* The fungus, *Trichoderma harzianum* E58 was obtained from the Forintek culture collection, grown in a 30 L fermenter, using 1% (w/v) Solka Floc B.W. 300 FC (Brown and Co., N.H., U.S.A.) as carbon source as described previously.

Bulk purification of xylanase: Seventeen liters of a 4 day old *Trichoderma harzianum* E58 culture was filtered through glass fiber paper to obtain the crude culture filtrate. The culture filtrate was ultrafiltered on a Pellicon apparatus (Millipore Ltd.) fitted with 0.47 m$^2$ of polysulfone membrane with a molecular weight cut-off of 10,000 daltons. Ultrafiltration was performed at approximately 6 and 45 L/h for the filtration and recirculation rates, respectively, until approximately 1 to 2% of the retentate remained. To obtain maximum recovery of retained protein, the membrane was flushed with 125 ml of 50 mM sodium citrate buffer, pH 4.8. The cellulase complex, which was retained, was concentrated by 40 to 60 fold, while 80% of the original xylanase was detected in the filtrate. The ultrafiltrate containing the xylanase enzyme was diluted with an equal volume of water, and the pH was adjusted to 4 with acetic acid. The xylanase enzyme was concentrated and solvent exchanged by binding to a cationic exchanger, SP-ZetaPrep 250 cartridge (7 cm diameter by 7 cm height) (AMF Molecular Separations Division, Meriden, Connecticut) equilibrated with 10 mM sodium acetate buffer, pH 4, at a flow rate of 7.5 L/h. The cartridge was washed with 2 L of 10 mM sodium acetate buffer, pH 4 and eluted with 2 L of 50 mM sodium phosphate, pH 8. Fractions of 250 ml were collected. The eluates were immediately titrated with acetic acid to pH 5.

Alternative methods of xylanase concentration: Ultrafiltration was performed with the Pellicon apparatus fitted with 0.47 m$^2$ of a cellulosic membrane with a molecular weight cut-off of 1,000 daltons. The filtration and recirculation rates were 0.9 and 9 L/h, respectively. Concentration by ammonium sulfate precipitation was carried out at 4° C. using an ammonium sulfate concentration of 20, 40, 60 and 80% saturation. The mixtures were stirred for 30 minutes and vacuum filtered via glass fibre discs. The discs containing the precipitated xylanase were mascerated in 5 ml of 50 mM sodium acetate, pH 4.8, stirred at 4° C. for 30 min and centrifuged at 10,000 g for 15 minutes. The supernatants were assayed for enzyme recovery. Ethanol and acetone precipitations were performed using final concentrations of 20, 40, 60 and 80% of the solvents pre-chilled to −60° C. Following the addition of the solvents, the mixtures were stirred at 4° C. for 1 minute and the precipitates were processed identically to those of the ammonium sulfate precipitates.

Assays: Xylanase and endoglucanase activities were assayed in 50 mM sodium citrate buffer, pH 4.8 at 50° C. One milliliter of an appropriately diluted enzyme was added to an equal volume of 1% (w/v) substrate and incubated for 30 minutes. Reducing sugar was determined by the 3,5-dinitrosalicylic acid method. Oat spelts xylan and carboxymethylcellulose (Sigma Chemicals) were used as substrates for the xylanase and endoglucanase assays respectively. Filter paper activity was assayed by the method of Mandels et al. Enzyme units were expressed as micromoles of D-xylose or D-glucose equivalents released per minute. Protein was determined by the method of Lowry, O. H., Rosebrough, N.J., Fan, A. C., and Randall, R. J. (1951) J. Biol. Chem. 193, 265-275 as modified by Tan, L. U. L., Chan, M. K.-H. and Saddler, J. N. (1984) Biotechnol. Lett. 6, 199-204.

The xylanase and cellulase enzyme components present in the culture filtrates of *Trichoderma harzianum* E58 were efficiently and rapidly separated by Pellicon ultrafiltration using a polysulfone membrane with a molecular weight cut-off of 10,000 daltons. The ability of the xylanases to penetrate this membrane was unique since their molecular sizes were between 20,000 and 29,000 daltons. The cellulase enzymes which were contained in the retentate, were concentrated between 40 and 60 fold, and were ideally suited for the hydrolysis of cellulose at high concentrations. The xylanase enzymes which were present in dilute solution in the ultrafiltrate, were concentrated and solvent exchanged by ion exchange chromatography using the cationic SP-ZetaPrep 250 cartridge. The Pellicon filtrate was diluted one fold prior to adsorption because the undiluted filtrate contained excessive salt concentrations which interfered with efficient binding. Elution of the column bound xylanase enzymes were carried out by a combination of increased ionic strength and increased pH in the buffer. The relatively low salt concentration and the use of the non-toxic salt, sodium phosphate, in the eluate negated the necessity to desalt the enzyme when it was used in conjunction with fermentative organisms. The eluted xylanase activity had a very high specific activity of approximately 2,100 IU/mg protein and was concentrated in the second and third fractions as shown in FIG. 1.

Figure 2:
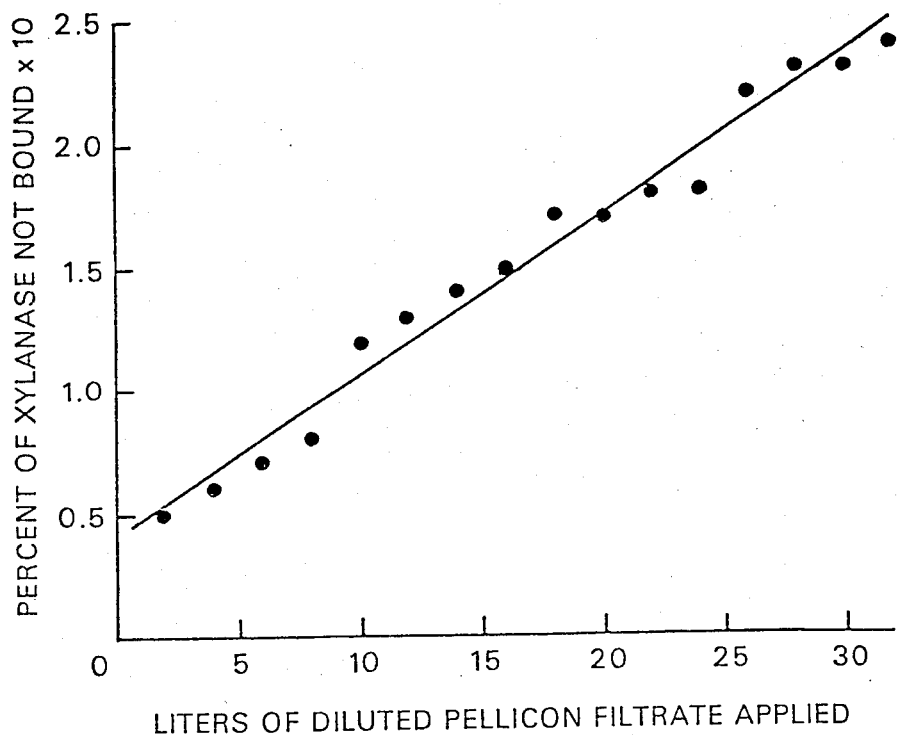
FIG. 2 shows the relationship between the percentage of initial xylanase activity which was not bound, and the volume of xylanase enzymes applied to the SP-ZetaPrep 250 column. The column was equilibrated with 10 mM sodium acetate buffer, pH 4. The xylanase enzymes applied to the column were the Pellicon Ultrafiltrate diluted with an equal volume of water. The pH of the enzyme solution was adjusted to 4 with acetic acid prior to application.

A comparison of different aliquots of the enzyme, before and after passage through the ion exchange column, showed that the percentage of xylanase which was not bound increased linearly with the volume of enzyme applied, up to a ratio of 0.25% as shown in FIG. 2. By taking the difference, it was apparent that more than 99.7% of the applied xylanase (3.3 g. protein, 6,070,000 IU) was bound. The recoveries of protein and xylanase activity were 100% and 132% respectively, if all the fractions containing xylanase activity were combined. The greater than 100% xylanase recovery may be due to the elimination of enzyme inhibitors in the Pellicon ultrafiltrate or the reported problems associated with the dinitrosalicylic acid reducing sugar assay (Robyt, J. F. and Whelan, W. J. (1972) Anal. Biochem. 45, 1121–1127).

Figure 3:
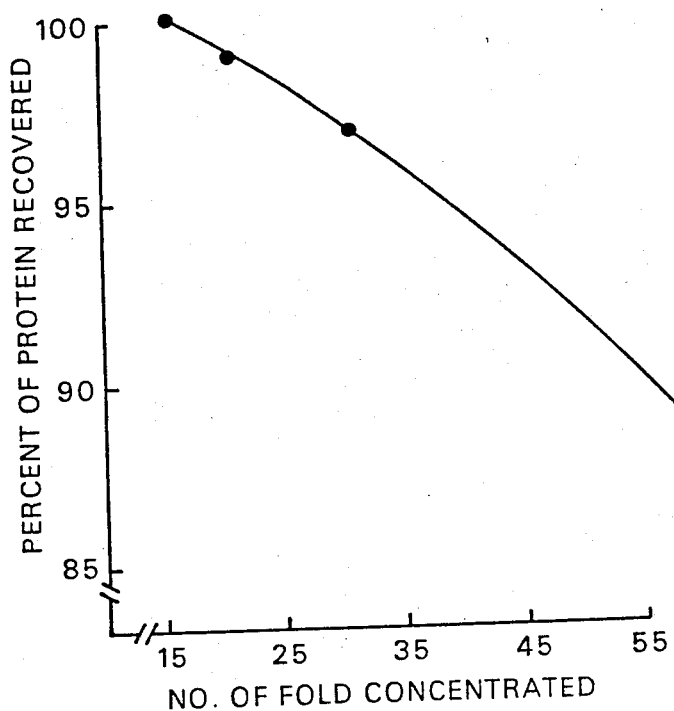
FIG. 3 shows the relationship between the percentage of protein recovered and the degree of concentration relative to the undiluted Pellicon ultrafiltrate. Various eluted fractions from the SP-ZetaPrep column were pooled and the total protein content was used in calculating the protein recovery. From left to right the points represented the pooling of: fractions 1-4; fractions 2-4; fractions 2 and 3 and fraction 2 alone.
Figure 4:
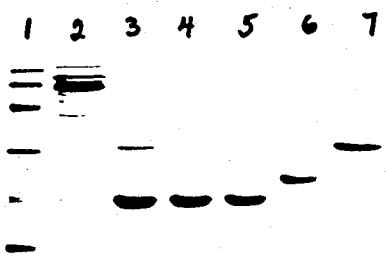
FIG. 4 shows sodium dodecyl sulphate polyacrylamide gel electrophoresis of xylanase preparations. Lane 1 contained the molecular weight standards corresponding to sizes of 94,000, 67,000, 43,000, 30,000, 20,100 and 14,400 daltons. Lanes 2 and 3 contained 50 $\mu$g of protein from the Pellicon retentate and Pellicon ultrafiltrate respectively. Fifty $\mu$g of xylanase enzymes concentrated by the ion exchange column was applied onto lane 4. Lanes 5-7 contained 30, 20 and 5 $\mu$g of purified xylanase enzymes with molecular weights of 20,000, 22,000 and 29,000 daltons respectively.

Since the objectives of the ion exchange step were to concentrate the xylanase enzyme, as well as to change the solvent in which the enzymes were dissolved, a plot of the protein recovery versus the degree of concentration was made as shown in FIG. 3. If fractions 2 and 3 were combined, a 31 fold increase in protein concentration was obtained while approximately 97% of the original protein was recovered. When the xylanase activity was assayed, a corresponding 41 fold increase in concentration was obtained while 127% of the original activity was recovered. The isolated xylanase was essentially pure as shown in FIG. 4 and was largely composed of the 20,000 and small amounts of the 22,000 dalton xylanases. These are the predominant xylanases found in *T. harzianum* culture filtrates. These partially purified xylanase preparation were shown to be compatible with the bacteria, *Klebsiella pneumoniae* could be used to produce 2,3-butanediol from aspenwood hemicellulose (Yu, E. K. C., Deschatelets, L., Tan, L. U. L. and Saddler, J. N. (1985) Biotechnol. Lett. June issue, 425–430). The 10,000 dalton cut-off polysulfone membrane in the ultrafiltration step was durable and was resistant to hydrolysis by the cellulase enzymes. The same membrane was used for over three years during which more than 20 runs were carried out without a significant deterioration of the membrane being observed. Since particulates were totally removed in the ultrafiltration step, the ultrafiltrate, containing the xylanase enzyme, was ideal for subsequent ion exchange treatment. As a result, column clogging was not a problem and the same colum was used for more than 10 runs without change of properties.

The above-described procedure for the production of cellulase-free xylanase has potential for scale-up studies. The ultrafiltration process has been proven to be cost effective on an industrial scale in comparison to other processes such as evaporation, lyophilization and salt and solvent precipitations. Scaling up of the ion exchange step using the SP-ZetaPrep cartridge has been claimed by the manufacturer (AMF Molecular Separations Division, Meriden, CT06450) to be straight forward. Industrial scale apparatus (multicartridge system) with a filtration rate of 720 L/h and a capacity to process kilogram quantities of protein is already available.

The efficiency of the ion exchange method for concentrating the xylanase enzyme in the ultrafiltrate was compared to other methods (Volesky, B and Luong, J. H. T. (1985) CRC Crit. Rev. Viotechnol. 2, 119–146) which are frequently used in industrial processes as shown in Table 1.

TABLE 1

| Comparison of Methods for Xylanase Concentration. | | | |
|---|---|---|---|
| Xylanase activity recovered (%) | | Processing[1] rate (L/h) | Reagents needed per[2] liter processed (g) |
| ion exchange | 127 | 2.7 | Na acetate (0.15) Na phosphate (0.36) Acetic acid (4.4) |
| Ultrafiltration | 93.7 | 0.8 | Na dodecyl sulfate (0.12) Na acetate (0.1) |
| Rotary evaporation | N.D. | 0.9 | None |
| Ammonium sulfate precipitation | 70 | N.D. | Ammonium sulfate (390) |
| Ethanol precipitation | 63 | N.D. | ethanol (3200) |
| Acetone precipitation | 55 | N.D. | Acetone (3200) |

[1]Average rate including the time needed for regeneration.
[2]Reagents needed for regenerating the apparatus are included.
N.D. Not determined.

Salt or solvent precipitation was found to result in poor enzyme recoveries of between 55 to 70%, probably because of the low initial protein concentration. When the large quantities of reagents needed for precipitation were taken into consideration, these processes were concluded to be economically nonviable processes. In addition, these processes result in the need for wastewater treatment, and/or devices for the removal of toxic and explosive vapors as well as explosive proof motors and switches. These capital expenditures all add to the cost of enzyme production. Xylanase enzymes concentrated by rotary evaporation were found to contain inhibitory substances which interfered with their utilization in combination with *K. pneumoniae* during the simultaneous hydrolysis and fermentation of various hemicellulose fractions. The need to dialyse the enzyme to remove these inhibitory materials would add another step to the process. Concentration by ultrafiltration was possible using the 1,000 dalton cut-off membrane, however the processing rate was less than one third that of the ion exchange method. In addition, the necessity to direct 90% of the flow into recirculation rather than filtration, as recommended by the manufacturer for the ultrafiltration process, ultimately resulted in higher capital costs for high output pumps and increased pumping costs. Such recirculation is not necessary in the ion exchange method so that pumping costs can be expected to be lower. The ion exchange method was found to have the highest processing rate when compared to the other concentration methods as well as resulting in the greatest percentage of xylanase activity recovered. The quantities of chemicals needed for column regeneration, enzyme and pH adjustments were small when compared with those for precipitation processes.

In conclusion, it has been shown that a highly purified xylanase system with high activity can be prepared in large quantities using relatively simple procedures.

Thus, the invention is composed of three components, the first component being the use of a hemicellulolytic microorganism such as *Trichoderma harzianum* E58, for the production of high levels of extracellular cellulase and xylanase enzymes. The second component is the discovery that the majority of xylanases can penetrate an ultrafiltration membrane having a molecular weight cut-off point of up to 20,000 daltons and preferably about 10,000 daltons which has lead to the use of an ultrafiltration step to separate the xylanase from the cellulase enzyme. Hitherto ultrafiltration membranes with a molecular weight cut-off point of 10,000 daltons have generally been accepted as a universal method for retaining proteins with enzymatic activities. The third component is the finding that xylanase in the ultrafiltrate can be efficiently absorbed to SP-ZetaPrep cartridges by first diluting the ultrafiltrate with water, followed by pH adjustment to between 3 and 5. Adsorbed xylanase can be concentrated and purified by subsequent elution with salt solutions with a pH between 7 and 10.

Although the present invention has been described with reference to preferred embodiments, workers skilled in the art will recognize that changes may be made in form and detail without departing from the spirit and scope of the invention.

What is claimed is:

1. A process for the separation of xylanase from a mixture thereof with cellulase, said mixture being produced by the culturing of a hemicellulolytic microorganism which comprises subjecting said mixture to ultrafiltration through an ultrafiltration membrane having a low molecular weight cutoff point between 1,000 and 20,000 daltons to obtain a xylanase rich ultrafiltrate and a cellulase rich retentate, and concentrating and purifying the ultrafiltrate by adsorption and elution from an insoluble matrix to produce a highly purified concentrated xylanase.

2. A process as claimed in claim 1, in which the insoluble matrix is a hydrophobic, anionic or cationic exchanger.

3. A process as claimed in claim 2, in which the exchanger is a cationic exchanger.

4. A process as claimed in claim 3, in which the ultrafiltrate may be diluted and the pH is adjusted to betweem 3–5 with acetic acid passed through an SP-Zeta-Prep column with a buffer between pH 3 to 5 and eluted with buffer between pH of 7 to 10.

5. A process as claimed in claim 1, 2 or 3, in which the membrane has a a low molecular weight cut-off point between 5,000 and 20,000.

6. A process as claimed in claim 1, 2 or 3 in which the membrane has a low molecular cut-off point, beteen 5,000 and 15,000.

7. A process as claimed in claim 1, 2 or 3, in which the membrane has a low molecular cut-off point, between 5,000 and 12,000.

8. A process as claimed in claim 1, 2 or 3, in which the membrane has a low molecular cut-off point, between 5,000 and 10,000.

9. A process as claimed in claim 1, 2 or 3 in which the membrane is a non-cellulosic membrane.

10. A process as claimed in claim 1, 2 or 3 in which the membrane is a polysulfone membrane.

11. A process as claimed in claim 1, 2, or 3, in which the microorganism is the fungus *Trichoderma harzianum* E58.

12. A process as claimed in claim 1, 2 or 3, in which the microorganism is the fungus *Trichoderma reesei*.

13. A process as claimed in claim 1, 2 or 3, in which the mixture is prepared by culturing *Trichoderma harzianum* E58 in a salt solution containing cellulose or hemicellulose as carbon source and subjecting the culture obtained to filtration or centrifugation to produce a culture filtrate.

* * * * *